(12) United States Patent
Gatto et al.

(10) Patent No.: US 7,667,066 B2
(45) Date of Patent: Feb. 23, 2010

(54) PREPARATION OF STERICALLY HINDERED HYDROXYPHENYLCARBOXYLIC ACID ESTERS

(75) Inventors: Vincent J. Gatto, Baton Rouge, LA (US); Hassan Y. Elnagar, Baton Rouge, LA (US); Chi Hung Cheng, Baton Rouge, LA (US); J. Robert Adams, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 369 days.

(21) Appl. No.: 10/788,850

(22) Filed: Feb. 27, 2004

(65) Prior Publication Data

US 2005/0192455 A1    Sep. 1, 2005

(51) Int. Cl.
*C07C 69/76* (2006.01)
*C07C 69/00* (2006.01)
(52) U.S. Cl. .......................................... 560/75; 560/130
(58) Field of Classification Search .................... 560/75, 560/130
See application file for complete search history.

(56) References Cited

U.S. PATENT DOCUMENTS

| | | | |
|---|---|---|---|
| 2,892,097 A | 6/1959 | Robertson | |
| 3,247,240 A | 4/1966 | Meier et al. | |
| 3,330,859 A | 7/1967 | Dexter et al. | |
| 3,364,250 A | 1/1968 | Dexter et al. | |
| 3,840,585 A | 10/1974 | Yamada et al. | |
| 4,049,713 A | 9/1977 | Spivack | |
| 4,085,132 A | 4/1978 | Park et al. | |
| 4,228,297 A * | 10/1980 | Haeberli et al. | 560/75 |
| 4,405,807 A | 9/1983 | Hasui et al. | |
| 4,536,593 A | 8/1985 | Orban et al. | |
| 4,582,618 A | 4/1986 | Davis | |
| 4,594,444 A | 6/1986 | Orban | |
| 4,659,863 A | 4/1987 | Burton | |
| 4,694,099 A | 9/1987 | Ahlfors et al. | |
| 4,716,244 A | 12/1987 | Orban | |
| 5,081,280 A | 1/1992 | Takee et al. | |
| 5,130,465 A | 7/1992 | Kovasy et al. | |
| 5,136,082 A | 8/1992 | Dang et al. | |
| 5,264,612 A * | 11/1993 | Evain et al. | 560/75 |
| 6,291,703 B1 | 9/2001 | Schaerfl, Jr. et al. | |
| 6,559,105 B2 | 5/2003 | Abraham et al. | |

OTHER PUBLICATIONS

Grant et al, Chemical Dictionary, McGraw-Hill Book Com, 5$^{th}$ ed. 1990, p. 11-12, (p. 3).*

* cited by examiner

*Primary Examiner*—Taylor Victor Oh
(74) *Attorney, Agent, or Firm*—James A. Jubinksy

(57) ABSTRACT

A novel manufacturing process is described for producing hindered phenolic alkyl esters, which may be useful as antioxidants. This process simplifies catalyst neutralization and removal during the preparation of hindered phenolic esters. Compositions that comprise the hindered phenolic esters produced according to these methods are also described.

50 Claims, No Drawings

PREPARATION OF STERICALLY HINDERED HYDROXYPHENYLCARBOXYLIC ACID ESTERS

BACKGROUND OF THE INVENTION (1) Field of the Invention

The present invention relates to a process for preparing a chemical composition, and more particularly, to a process for preparing sterically hindered hydroxyphenylcarboxylic acid esters, as well as to compositions containing the same.

(2) Description of Related Art

Many organic materials, such as polymers, fuels, and lubricants, are susceptible to oxidative and thermal deterioration from the action of heat, mechanical stress, and chemical reagents (such as atmospheric oxygen or metallic impurities). Deterioration of lubricants may result in an increase in their total acidity, formation of gums, discoloration, loss of physical properties such as viscosity, decreased potency, increasing molecular weight, polymerization, and the creation of odor. Changes in these properties can cause the lubricant to lose its effectiveness and longevity.

Oxidative degradation of a lubricant is a sequential process involving initiation, propagation, and termination phases. The initiation phase can begin by the formation of free radicals, which may be produced in a number of ways. For example, free radicals may be formed by reactive peroxides that are present during production of the lubricant, by thermal, mechanical or radiation stresses that occur during processing or end use, or by chemical reactions with impurities contained in the lubricant.

During the propagation phase, the free radicals can react with oxygen to form peroxy ($RO_2$) and alkoxy (RO) radicals which, in turn, may abstract hydrogen from the lubricant to form unstable hydroperoxides ($RO_2H$), alcohols (ROH), and new hydrocarbon free radicals (R). These free radicals can once again combine with oxygen to continue the oxidative cycle until the process slows or stops completely during the termination phase.

Lubricants are also subject to thermal degradation when used during periods of elevated temperatures or during periods of rapid cycling between elevated and low temperatures. Thermal degradation of a lubricant results in the disruption of long-chain hydrocarbons and causes the formation of unstable hydrocarbon compounds. These unstable compounds are especially prone to oxidation and can polymerize to form resins and sludge in the lubricant. For example, as an engine goes through multiple heating and cooling cycles, this sludge can harden and cause problems such as restricted passageways and decreased component tolerances.

One way to interrupt these destructive processes is to incorporate a stabilizer such as an antioxidant into the lubricant composition. Generally known antioxidants, such as hindered phenolic compounds, may be used to retard thermal and oxidative degradation. Such hindered phenolic compounds donate an active hydrogen atom to the oxidative free radicals formed during the initiation and propagation phases to ensure that the termination phase is reached quickly.

Unfortunately, while hindered phenol antioxidants are effective for combating the destructive effects of oxidation and thermal breakdown in lubricants, they are notoriously difficult to synthesize efficiently and in highly pure form. Conventional methods for the production of hindered phenol derivatives, particularly esters of phenols, often involve costly and time-consuming multi-step reaction procedures. These procedures usually require complicated isolation procedures for distilling the hindered phenol methyl ester intermediate and/or time-consuming and costly water washing steps to remove the unused or used catalysts (referred to herein as "catalyst residue") during the production process.

For example, typical methods for preparing some hindered phenol antioxidants involve a Michael reaction between alkylphenols and an alkyl acrylate such as methyl acrylate, followed by extensive water washing and isolation of the resultant intermediate ester. Michael reactions are base-catalyzed conjugate additions of carbon nucleophiles (donors) to activated unsaturated compounds (acceptors). For the preparation of antioxidants, the Michael reaction donor is usually an alkylphenol compound and the acceptor is an unsaturated alkyl acrylate.

After formation of the intermediate ester through the Michael reaction, the intermediate ester is then subjected to a second step involving transesterification, followed once again by extensive washing and then purification of the solid antioxidant. Typically, the solid product is purified by crystallization and filtration.

In some methods, the separate transesterification step can be omitted if a suitable alcohol is incorporated into the alkylphenol/alkyl acrylate reaction. While such single-step reactions have advantages over multi-step preparation methods, such single-step reactions continue to have their disadvantages, particularly with respect to end-product purity.

To accelerate reaction rates, a base catalyst is usually added during both the Michael reaction and transesterification steps. Often, different catalysts at each step must be employed to achieve acceptable reaction times. Before the final antioxidant product can be isolated, however, all of the catalyst residue must be removed or the catalysts will contaminate the resulting antioxidant and, therefore, any lubricant made with the antioxidant.

Typically, the base catalysts are removed by first neutralizing them with acids such as acetic, hydrochloric or sulfuric. The antioxidant product is then precipitated away from the catalyst and filtration is used to separate the final product from the catalyst. However, catalysts are difficult to remove and cannot always be removed completely from the final product. In particular, while filtration may be suitable for the preparation of solid antioxidants, it is inappropriate and impractical for purifying liquid antioxidants.

One way to assist in the catalyst removal is through the use of extensive water washings of the reaction products at the end of each step. However, water washes slow down the overall time required to complete the antioxidant synthesis and add greatly to the inefficiency of these processes. Other reported methods to neutralize the catalyst generate large amounts of byproduct solids and lead to a waste disposal issue.

Improvements have been sought in many different reported procedures for producing a hindered phenolic compound. These procedures, however, do not adequately address all of the problems that arise from the making of hindered phenolic compounds.

For example, U.S. Pat. No. 4,085,132 to Park, et al. describes a one-step method of producing higher molecular weight hindered phenolic esters. According to this method, methyl acrylate is gradually added to a reaction mixture comprising 2,6-di-tert-butylphenol (which is a higher molecular weight monohydric hindered phenol), a high molecular weight alcohol, and a catalyst, without isolating the intermediate in a separate step. Higher excesses of methyl acrylate are required in order to drive this type of reaction to completion. The catalysts employed are alkaline metal catalysts of lithium, sodium and potassium. Catalyst neutralization is performed with acetic acid, which may not be effective for a water wash-free product isolation. The hindered phenol ester product is isolated as a solid by crystallization or recrystallization from the neutralized reaction mixture.

While such a method works well for solids, it is inappropriate and impractical for washing liquid hindered phenol products. Moreover, this type of isolation leads to significant yield loss of product in the filtrate and can result in high levels of impurities.

U.S. Pat. No. 4,228,297 to Haeberli, et al., on the other hand, describes one of the two-step methods where the Michael reaction is performed with one catalyst and the transesterification reaction is performed with a second catalyst that has a different chemical composition than the first catalyst. Again, the hindered phenol ester product is isolated as a solid by crystallization from the neutralized reaction mixture. All neutralizations are performed with acetic acid and all products are isolated by filtration. Again, this method is not practical for production and purification of liquid hindered phenol products.

Another example of a one-step reaction is set forth in U.S. Pat. No. 3,840,585 to Yamada, et al., wherein an alkyl acrylate is reacted with an alkylphenol to produce the final product. The patent describes the use of complex metal hydrides as catalysts. Such complex metal hydrides are very difficult to handle and to remove from the product but the process attempts to remove them by using acetic acid for neutralization. The reaction requires a promoter that is removed from the finished product by diluting the product with large volumes of toluene and then subsequently washing with water.

A method for the production of a hindered phenol methyl ester by the very rapid addition of methyl acrylate to the alkylphenol starting compound is described in U.S. Pat. No. 4,659,863 to Burton. However, hindered phenol alkyl ester products are not isolated in this patent. Acids that are suitable for catalyst neutralization according to this patent are acetic acid, hydrochloric acid and sulfuric acid.

U.S. Pat. No. 3,247,240 to Meier, et al., describes using alkali metal bases as catalysts in the Michael reaction. A variety of alkyl acrylates are used and all of the examples demonstrate higher alcohol products isolated by crystallization. The methyl ester is isolated by distillation and the reaction mixtures are neutralized with hydrochloric acid, followed by water washes. Distillation and crystallization processes are costly, time consuming, and lead to yield losses.

The one-step production method described in U.S. Pat. No. 3,364,250 to Dexter, et al., creates hindered phenolic compounds by substituting a higher alkyl acrylate for methyl acrylate. The catalyst is neutralized with hydrochloric acid and then removed through water wash steps and a distillation step. The hindered phenol product is isolated as a solid by crystallization from the neutralized reaction mixture.

Another method for producing a hindered phenol methyl ester is described in U.S. Pat. No. 3,330,859 to Dexter, et al. The two-step method involves purification by distillation through which the higher alkyl esters are crystallized as a solid and then catalyst neutralization is carried out with acetic and hydrochloric acid. This method is inappropriate for liquid transesterified hindered phenolics.

Finally, U.S. Pat. No. 6,559,105 to Abraham, et al., describes a Michael reaction that uses large amounts of magnesium silicate as an absorbent and filter aid to neutralize the potassium hydroxide catalyst. This process creates waste disposal issues due to the large volume of solids that are generated. For example, approximately 2.70% solids based on the weight of total phenolic ester product are produced.

There are also several process patents that describe specifically the transesterification step, including, for example, U.S. Pat. No. 6,291,703 to Schaerfl, et al., U.S. Pat. No. 4,694,099 to Ahlfors, et al., U.S. Pat. No. 5,081,280 to Takee, et al., U.S. Pat. No. 5,136,082 to Dang, et al., U.S. Pat. No. 2,892,097 to Robertson, U.S. Pat. No. 4,594,444 to Orban, U.S. Pat. No. 4,536,593, and U.S. Pat. No. 4,716,244 to Orban.

The use of two different catalysts in such prior art processes is costly and ultimately requires the removal of both catalysts. Typically, these processes require repeated water washes to adequately remove the catalyst residue and purify the final product. Therefore, such processes are time-consuming.

While one might believe that time can be saved by employing one of the prior art single-step processes where the transesterification reaction and the Michael reaction are carried out in the same reaction mixture, these processes generally result in longer overall reaction times. Moreover, in these simultaneous, single-step, reactions, larger excesses of methyl acrylate are required to run the reaction and a lower purity product is generally obtained.

From the foregoing, it can be seen that a need exists for improved and more efficient methods for producing hindered phenols and, particularly, for producing sterically hindered phenol esters that can be used as antioxidants in compositions such as lubricants. It would also be useful to provide improved methods for producing hindered phenol antioxidants that do not rely on multiple catalyst additions and that do not require extensive water washing or difficult phase separation steps. Likewise, methods that offer improved processes for reducing the concentration of catalysts in the final hindered phenol product would also be desirable in that such products could be utilized as antioxidants for use in improved compositions such as better-formulated lubricants.

SUMMARY OF THE INVENTION

Briefly, the invention is directed to novel low cost and low waste manufacturing processes for producing hindered phenolic alkyl ester compounds. In general, several processes can be employed for producing the hindered phenolic alkyl ester compounds.

For example, one two-step process involves reacting an alkyl acrylate, such as methyl acrylate, with an alkylphenol compound in the presence of a first catalyst to form a methyl ester intermediate compound, then reacting an alcohol having at least 2 carbon atoms with the methyl ester intermediate compound in the presence of a second catalyst to form the hindered phenolic alkyl ester compound, neutralizing any catalyst residue with an aqueous phosphoric acid so as to form a precipitated phosphate salt, and then separating the precipitated phosphate salt from the hindered phenolic alkyl ester compound. In one particular embodiment of this process, the first and second catalysts may have the same chemical composition and in other embodiments, the first and second catalysts may be different in that they have different chemical compositions. In still other embodiments, the second catalyst is not an additionally added catalyst but is instead merely a remainder of the first catalyst that is employed during the Michael reaction step involving the reaction of the alkyl acrylate and the alkylphenol. That is, the catalyst in the first Michael reaction is carried over, unaltered, and used to catalyze the second transesterification reaction. In this manner, the first catalyst is also used as the second catalyst during the reaction of the alcohol with the methyl ester intermediate compound.

In another example, a hindered phenolic alkyl ester compound is produced by reacting methyl acrylate with an alkylphenol compound in the presence of a first catalyst to form a methyl ester intermediate compound. An alcohol is then reacted with the methyl ester intermediate compound in the presence of a second catalyst to form the hindered phenolic alkyl ester compound. In this particular embodiment, the second catalyst has the same chemical composition as the first catalyst and the catalysts are neutralized with an aqueous acid, which may or may not be phosphoric acid, to form a precipitated salt. Finally, the precipitated salt is separated from the hindered phenolic alkyl ester compound by filtration or decantation.

Again, in certain embodiments of this reaction, the remainder of the first catalyst employed in the Michael reaction may be employed as the second catalyst in the transesterification reaction.

As mentioned, the aqueous acid employed in this particular process may be selected from the group consisting of sulfuric acid, nitric acid, hydrobromic acid, hydroiodic acid, hydrochloric acid, formic acid, acetic acid, phosphoric acid, and mixtures thereof.

In another embodiment, a hindered phenolic alkyl ester compound may be produced in a single-step reaction by first reacting an alkyl acrylate with an alkylphenol compound in the presence of a catalyst to form the hindered phenolic alkyl ester compound and then neutralizing the catalyst residue with an aqueous phosphoric acid so as to form a precipitated phosphate salt. The precipitated phosphate salt is then separated from the hindered phenolic alkyl ester compound by filtration or decantation.

The compositions made according to the present process are particularly useful as antioxidants for lubricant compositions. In particular, lubricants such as passenger car engine oils, heavy duty diesel engine oils, railroad oils, natural gas engine oils, turbine oils, rust oils, oxidation oils, slideway oils, hydraulic oils, industrial oils, automotive gear oils, automatic transmission fluids and manual transmission fluids, tractor fluids, universal tractor fluids and hydraulic fluids, power steering fluids, gear lubricants, industrial oils, pump oils, and mixtures thereof, may all take advantage of the antioxidizing properties available from the presently-produced products.

The inventive processes generally produce purified hindered phenolic esters, yet allow for the elimination of methyl ester intermediate purification, the use of the same catalyst (when two reactions are employed in the process), and elimination of the costly and time consuming water wash steps that have historically been used to remove catalyst residues.

Use of phosphoric acid in certain embodiments to neutralize the catalyst residue also simplifies the catalyst removal process by allowing for filtration of the resulting metal phosphate salts formed by reaction of the catalyst with the phosphoric acid. Finished hindered phenolic ester products having less than 200 ppm catalyst and less than 20 ppm phosphorous may typically be produced according to the present processes.

DETAILED DESCRIPTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

In accordance with the present invention, it has been discovered that hindered phenolic compounds can be made according to the methods described herein. The phenolic compounds produced thereby make excellent antioxidants suitable for stabilizing organic materials, such as lubricants, that are sensitive to oxidative and/or thermal degradation.

Generally speaking, high molecular weight hindered phenols are among the applicable antioxidants synthesizable according to the methods described herein. As used herein, the term "hindered phenol" or "hindered phenolic compound" refers to a phenol compound substituted with one or more substituent groups at its benzene ring. Hindered phenols are well known to those skilled in the art and may be characterized as phenolic compounds, which also contain sterically bulky radicals in close proximity to the phenolic hydroxyl group.

By way of example, tertiary butyl groups may be substituted onto the benzene ring in at least one of the ortho positions relative to the phenolic hydroxyl group. The presence of these sterically bulky substituted radicals in the vicinity of the hydroxyl group serves to retard the hindered phenol's stretching frequency and, correspondingly, its reactivity. This steric hindrance provides the phenolic compound with its stabilizing properties when it acts as an antioxidant.

The hindered phenolic esters of the present invention can be prepared by several different methods. One such method involves a two-step reaction. The first step is a Michael reaction of a hindered phenol such as 2,6-di-tert-butylphenol with an alkyl acrylate such as methyl acrylate in the presence of a catalyst and, optionally, a promoter, to produce an intermediate phenol alkyl ester. The second step is a transesterification reaction between the intermediate phenol alkyl ester and an alcohol. This aspect of the present invention employs the same type of catalyst in both the Michael and in the transesterification reaction, either as two separately-added catalysts or as a single-added catalyst that is used in the first reaction and is then carried over for use in the second reaction.

Utilization of the same type of catalyst in both the transesterification and Michael reactions that occur during formation of the hindered phenolic esters in a two-step process represents an improvement over known processes. As mentioned previously, many prior two-step processes utilize different catalysts for the transesterification and Michael reactions. Other prior processes may utilize the same catalysts for both reactions, but these processes allow the transesterification and Michael reactions to occur at the same time in a single-step process. When these processes are conducted, the attendant disadvantages discussed above result. In particular, as previously suggested, both of these prior art processes are undesirable from an efficiency and product purity standpoint.

In addition, in the present invention, the catalyst is removed by first neutralizing with an aqueous acid, such as aqueous phosphoric acid, and then removing excess water, and, finally, filtering to remove the precipitated phosphate salts. By removing the catalyst in this fashion, the present invention eliminates the need for water wash and slow phase separation steps and avoids having to purify the final product through distillation, which allows for a shortening of the overall process completion time.

Additionally, the removal of the aqueous acid-precipitated catalyst by means of a filtration step allows the process to occur while the hindered phenol antioxidants are in a liquid state. This is an improvement over conventional processes which typically do not allow for the production and purification of hindered phenol antioxidants in a liquid form.

Finally, by removing the catalyst through a neutralization step with an aqueous acid such as phosphoric acid, the total amount of waste solids produced is less than the amount created through known process. For example, the methods of the present invention typically generate waste solids on the order of between about 0.65% and 1.02% by weight based on the phenolic ester product. By comparison, other reported methods generate as much as 2.70% solids.

The Michael reaction is performed, in one embodiment, by adding methyl acrylate to a solution of a hindered phenol (e.g., an alkylphenol such as 2,6-di-tert-butylphenol), a promoter and a catalyst in a reaction vessel. For example, a reaction quantity of an alkylphenol, such as 2,6-di-tert-butylphenol, is heated to between about 60° C. and 65° C. or higher under vacuum to purge oxygen from the reaction vessel. The entire reaction may be carried out in an atmosphere of inert gas such as a partial or full nitrogen atmosphere.

If the alkylphenol is in a solid form prior to being used in the process, it is first melted in order to render it liquid. After the alkylphenol is melted, the desired catalyst is then added. Next, an optional promoter may be added. Optionally, water added to the reaction with the catalyst may be removed by distillation, by vacuum distillation, or as a toluene azeotrope prior to the Michael addition step. This can be accomplished by adding toluene to the alkylphenol and heating the mixture to between about 130° C. and about 160° C. and collecting the water/toluene azeotrope in a Dean-Stark trap. The mixture is then heated to a reaction temperature and the methyl acrylate is added. The reaction is generally conducted at a temperature of between 80° C. and 150° C. and, more particularly, to a temperature between 100° C. and 130° C.

Generally, about equimolar portions of methyl acrylate and alkylphenol reactants are used, with the overall molar ratio of methyl acrylate to alkylphenol typically being at least about 1:1. However, either of the methyl acrylate or alkylphenol may be used in excess according to the process of the invention. In certain embodiments, a slight excess of methyl acrylate may be employed so that the molar ratio of methyl acrylate to alkylphenol is between about 1.05:1 to about 1.30:1 (i.e., so that the methyl acrylate molar excess is between about 5% and about 30% above the molar amount of the alkylphenol). In certain embodiments, a slight excess of alkylphenol may be employed so that the molar ratio of alkylphenol to methyl acrylate is between about 1.05:1 to about 1.30:1 (i.e., so that the alkylphenol molar excess is between about 5% and about 30% above the molar amount of the methyl acrylate). For example, in one embodiment, an alkyl phenol molar excess of about 10% to about 15% can be used.

The time for addition of the methyl acrylate is not critical to the operability of the present invention and can be carried out over a time period of between about 15 minutes and about 8 hours. After the methyl acrylate addition is complete, the reaction is then extended for an additional 1 to 24 hours, depending on the reaction temperature selected. One skilled in the art will understand that lower reaction temperatures will require longer reaction times. The reaction is considered complete when less than 2 weight % ("wt. %"), or in some embodiments less than 1 wt. %, of the starting hindered phenol reactant remains.

By way of example, the product of a Michael reaction between methyl acrylate and 2,6-di-tert-butylphenol is the hindered phenol methyl ester intermediate, 3,5-di-tert-butyl-4-hydroxyhydrocinnamic acid, methyl ester.

The transesterification reaction is carried out by reacting the chosen molecular weight alcohol with the hindered phenol methyl ester intermediate produced in the Michael reaction. The transesterification reaction converts the methyl ester intermediate to a higher molecular weight alkyl ester. The transesterification reaction is performed at a temperature sufficient to collect the methanol by-product and to drive the reversible reaction to completion.

During the transesterification reaction, a catalyst can also be present to accelerate the reaction. The chemical composition of the catalyst used in the transesterification reaction has desirably the same chemical composition as the catalyst used in the Michael reaction. This can be achieved by simply not washing or not purifying away the first catalyst addition to the Michael reaction and then, optionally if necessary, adding back to the reaction mixture some of the same catalyst. In the alternative, this can be achieved by purifying away the first catalyst addition during the Michael reaction, and subsequently, adding back the identical type of catalyst to the transesterification reaction. Keeping the catalyst the same between the Michael reaction and the transesterification reaction improves the overall efficiency and quality of the production, while at the same time reducing costs.

By way of example, the reaction of 3,5-di-tert-butyl-4-hydroxyhydrocinnamic acid, methyl ester with 2-ethylhexanol will produce 3,5-di-tert-butyl-4-hydrohydroxycinnamic acid, 2-ethylhexyl ester. In this reaction, it is advantageous to use alcohols between certain molecular weight ranges. For example, alcohols that have low boiling points are difficult to drive the reaction to completion. Thus, the transesterification reaction of the present invention typically uses high molecular weight alcohols. As used herein, the terms "high molecular weight alcohol" refer to alcohols that are at least about a $C_5$ alcohol or greater (e.g., alcohols that have at least 5 carbons or more). In some embodiments, the alcohol is a $C_5$-$C_{25}$ alcohol.

Suitable alcohols for the reaction include, but are not limited to, primary, secondary or tertiary alcohols that can be linear or branched alcohols. Other alcohols include the polyhydric alcohols. By way of example, alcohols that are suitable for use with the present invention may comprise at least one alcohol that is selected from the group consisting of hexanol, heptanol, octanol, nonanol, decanol, undecanol, dodecanol, tridecanol, tetradecanol, cosanol, docosanol, tricosanol, tetracosanol, pentacosanol, hexacosanol, heptacosanol, linear and branched forms thereof, and mixtures thereof.

The transesterification reaction can be conducted at elevated pressures, normal atmospheric pressure, or sub-atmospheric pressures. In general, the transesterification reaction may be conducted at sub-atmospheric pressures, for example, in the range of from about 1 mm Hg to about 400 mm Hg. In this way, the vaporization of the lower alkanol (e.g., methanol) formed is facilitated during the course of the transesterification reaction. Removal of the lower alkanol during transesterification helps to drive the transesterification reaction towards completion.

In one embodiment, the two-step method of the present invention provides a method for the production of a hindered phenolic alkyl ester compound that includes reacting methyl acrylate with an alkylphenol compound in the presence of a first catalyst to form a methyl ester intermediate compound, reacting an alcohol having at least 2 carbon atoms with the methyl ester intermediate compound in the presence of a second catalyst to form the hindered phenolic alkyl ester compound, neutralizing the catalyst residue with an aqueous phosphoric acid so as to form a precipitated phosphate salt, and separating the precipitated phosphate salt from the hindered phenolic alkyl ester compound.

In other embodiments, the two-step method of the present invention provides a method for the production of a hindered phenolic alkyl ester compound that includes reacting methyl acrylate with an alkylphenol compound in the presence of a first catalyst to form a methyl ester intermediate compound, reacting an alcohol having at least 2 carbon atoms with the methyl ester intermediate compound in the presence of a second catalyst to form the hindered phenolic alkyl ester compound, wherein the second catalyst has the same chemical composition as the first catalyst, neutralizing the first and second catalysts with an aqueous acid so as to form a precipitated salt, and separating the precipitated salt from the hindered phenolic alkyl ester compound.

In still other embodiments, the two-step method of the present invention provides a method for the production of a hindered phenolic alkyl ester that avoids the need for a water wash step or a distillation step. For example, in this embodiment, the method essentially includes only the following steps: reacting methyl acrylate with an alkylphenol compound in the presence of a first catalyst to form a methyl ester intermediate compound, reacting an alcohol having at least 2 carbon atoms with the methyl ester intermediate compound in the presence of a second catalyst to form the hindered phenolic alkyl ester compound, wherein the second catalyst has the same chemical composition as the first catalyst, neutralizing the first and second catalysts with an aqueous acid so as to form a precipitated salt, and separating the precipitated salt from the hindered phenolic alkyl ester compound.

The two-step production method of the present invention also provides a method for the production of a hindered phenolic alkyl ester compound having the structure according to Formula I:

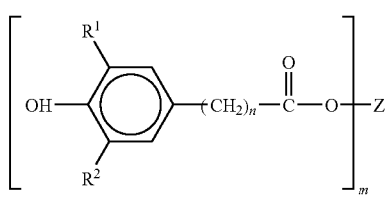
(I)

wherein:

$R^1$ and $R^2$ are independently selected from the group consisting of H, alkyl, cycloalkyl, aryl, alkylaryl, and arylalkyl;

n is 2;

m is 1, 2, 3, or 4; and

Z is alkyl;

comprising the steps of:

a) reacting methyl acrylate with an alkylphenol compound in the presence of a first catalyst to form a methyl ester intermediate compound, wherein the alkylphenol compound has the structure according to Formula II:

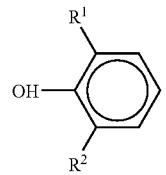
(II)

and wherein $R^1$ and $R^2$ are defined as above;

b) reacting an alcohol having at least 2 carbon atoms with the methyl ester intermediate compound in the presence of a second catalyst to form the hindered phenolic alkyl ester compound having the structure according to Formula I;

c) neutralizing the catalyst residue with an aqueous phosphoric acid so as to form a precipitated phosphate salt; and d) separating the precipitated phosphate salt from the hindered phenolic alkyl ester compound.

In one embodiment, $R^1$ and $R^2$ are both alkyl. In another embodiment, $R^1$ and $R^2$ are independently selected from butyl and $C_1$-$C_6$ alkyl. In yet another embodiment, $R^1$ and $R^2$ are t-butyl.

Alternatively, Z is a $C_1$-$C_{10}$ alkyl, and in further embodiments, Z is selected from the group consisting of methyl, ethyl, propyl, butyl, hexyl, heptyl, isoheptyl, octyl, isooctyl, and 2-ethylhexyl.

As used herein, when the term "alkyl" is used, either alone or within other terms such as "haloalkyl" and "alkylsulfonyl"; it embraces linear or branched radicals composed of carbon atoms. The number of carbon atoms can also be expressed as "$C_1$-$C_5$,", for example. Examples of such radicals include methyl, ethyl, n-propyl, isopropyl, n-butyl, isobutyl, sec-butyl, tert-butyl, pentyl, isoamyl, hexyl, octyl and the like. When an alkyl radical, such as, for example, "butyl" is used, it is intended that all primary, secondary and tertiary forms of the alkyl radical are encompassed by the term, including n-butyl, t-butyl, isobutyl and sec-butyl.

The terms "hydrido", "—H", or "hydrogen", denote a single hydrogen atom (H). This hydrido radical may be attached, for example, to an oxygen atom to form a hydroxyl radical, or two hydrido radicals may be attached to a carbon atom to form a methylene (—$CH_2$—) radical.

The term "aryl", alone or in combination, means a carbocyclic aromatic system containing carbon rings wherein such rings may be attached together in a pendent manner or may be fused. The term "aryl" embraces aromatic radicals such as phenyl, naphthyl, tetrahydronapthyl, indane, and biphenyl.

The terms "aralkyl", or "arylalkyl" embrace aryl-substituted alkyl radicals such as benzyl, diphenylmethyl, triphenylmethyl, phenethyl, and diphenethyl.

In the naming of substituent groups for general chemical structures, the naming of the chemical components of the group is typically from the terminal group-toward the parent compound unless otherwise noted, as discussed below. In other words, the outermost chemical structure is named first, followed by the next structure in line, followed by the next, etc. until the structure that is connected to the parent structure is named.

In another embodiment, the present invention provides a two-step method for the production of a hindered phenolic alkyl ester compound having the structure according to Formula I:

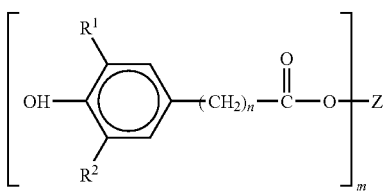

wherein:
R¹ and R² are independently selected from the group consisting of H, alkyl, cycloalkyl, aryl, alkylaryl, and arylalkyl;
n is 2;
m is 1, 2, 3, or 4; and
Z is alkyl;

comprising the steps of:

a) reacting methyl acrylate with an alkylphenol compound in the presence of a first catalyst to form a methyl ester intermediate compound, wherein the alkylphenol compound has the structure according to Formula II:

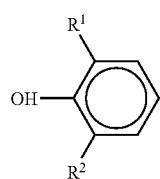

and wherein R¹ and R² are defined as above;

b) reacting an alcohol having at least 2 carbon atoms with the methyl ester intermediate compound in the presence of a second catalyst to form the hindered phenolic alkyl ester compound having the structure according to Formula I, wherein the second catalyst has the same chemical composition as the first catalyst;

c) neutralizing the first and second catalysts with an aqueous acid so as to form a precipitated salt; and d) separating the precipitated salt from the hindered phenolic alkyl ester compound.

Another method suitable for use as the present invention involves reacting an alkylphenol, such as 2,6-di-tert-butylphenol, with a specific alkyl acrylate in the presence of a catalyst, an alcohol and, optionally, a promoter in one step. The catalyst is then neutralized with an aqueous acid such as phosphoric acid so as to form a precipitated salt which is then separated from the ester. In this method, the product produced is the final product, thus eliminating the need for a transesterification reaction step.

For this "one-step" reaction, the same catalysts and promoters can be used as those described for the "two-step" methyl acrylate reaction. In one embodiment, the alkyl acrylate that is suitable for the one-step reaction is methyl acrylate. In other embodiments, the alkyl acrylates that are suitable for the one-step reaction are those alkyl acrylates that are high molecular weight acrylates having a higher molecular weight than methyl acrylate. As used herein, the terms "high molecular" or "higher molecular" with respect to the weight of an alkyl compound means that the alkyl chain is longer than methyl. For example, in one embodiment, linear or branched higher molecular weight alkyl acrylates such as $C_2$-$C_{24}$ alkyl acrylates are suitable for use with the presently described "one-step" method. By way of example, such higher molecular weight acrylates include, but are not limited to, ethyl acrylate, propyl acrylate, n-butyl acrylate, sec-butyl acrylate, 2-ethylhexyl acrylate, isooctyl acrylate, and the like.

In some embodiments, the high molecular weight acrylates are linear or branched $C_2$-$C_{10}$ alkyl acrylates, and other embodiments, the $C_2$-$C_{10}$ alkyl acrylates comprise at least one compound that is selected from the group consisting of n-butyl acrylate, sec-butyl acrylate, n-octyl acrylate, 2-ethylhexyl acrylate, isoheptyl acrylate, isooctyl acrylate, isononyl acrylate, isodecyl acrylate, and mixtures thereof.

Generally speaking, the catalysts employed in the present processes may include, but are not limited to, alkali and alkaline earth metal hydroxides and oxides including, but not limited to, potassium hydroxide, sodium hydroxide, lithium hydroxide, cesium hydroxide, calcium hydroxide, and magnesium hydroxide. Other suitable catalysts include, but are not limited to, alkali metal hydrides, alkali metal alkoxides, alkali metal amides, dibutyltin oxide, zinc salts, calcium salts, monoalkyltins, alkali metal hydrocarbyloxides, and mixtures thereof.

The amount of alkali metal hydroxide catalyst used typically is based on the total amount of active hydrogens in the reactive hindered phenolic mixture. For example, although the catalysts may be employed in amounts ranging from 0.001 to 10 mole % based on the alkylphenol compound, amounts of from about 1 to 5 mole % are usually employed, and, in some embodiments, about 2.5 mole % is employed.

The neutralization step may be carried out in some embodiments with an aqueous acid and in some embodiments with a specific aqueous acid such as aqueous phosphoric acid. In some embodiments, concentrated phosphoric acid (14.6 M) is first diluted with water to make a diluted aqueous solution of phosphoric acid before adding the acid. Dilutions of concentrated phosphoric acid with water can range anywhere from 5% to 95% aqueous phosphoric acid. Other suitable dilutions can range from 10% to 80% aqueous phosphoric acid, and in some embodiments, the dilution can range from 17% to 20% aqueous phosphoric acid. The application of aqueous phosphoric acid in the present invention promotes the formation (i.e., precipitation) of crystalline metal phosphate salts that are easily removable from the final product by filtration.

The amount of aqueous acid (e.g., phosphoric acid) that is added to the reaction for catalyst neutralization is based on the amount of catalyst used which, in turn, corresponds to the amount of catalyst residue that is to be neutralized. In general, the reaction mixture contains a molar equivalent of the aqueous acid that is between about 30% and 200% the molar equivalent of the catalyst, and often the molar equivalent of the aqueous acid is between about 50% and 100% the molar equivalent of the catalyst. In many cases, the reaction mixture contains a molar equivalent of the aqueous acid that is between about 65% and about 95% the molar equivalent of the catalyst.

The aqueous acid should be added to the hindered phenol alkyl ester reaction mixture when the mixture is at a temperature of between about 50° C. and about 150° C., and typically, the aqueous acid is added to the reaction mixture when the mixture is at a temperature of about 100° C. The rate of aqueous acid addition is not critical to the process disclosed herein and will necessarily be adjusted based on the effectiveness of the neutralization reaction.

For most reactions, the catalyst neutralization reaction is allowed to proceed for at least one hour, and in some cases, the neutralization proceeds for between about 2 and 3 hours.

Completion of the catalyst neutralization can often be judged by the color change of the reaction mixture from an orange red to a yellow color.

After the aqueous acid addition, the added water is removed by atmospheric distillation or vacuum distillation. As the added water is removed, the metal salts of the catalyst are formed (e.g., potassium phosphate). The resulting metal salts are often insoluble even in the hot phenolic adducts. The resulting salts are then separated away from the desired product by known methods including, but not limited to, filtration, centrifugation, decantation, and the like. A filter aid such as Celite® (e.g. Celite 545, Baker Analyzed Reagent) may be used to improve the rate of separation and the efficiency of metal salt removal.

The process of the present invention produces a product that contains low levels of metal salts/ions, which may remain after neutralization of the base catalyst with an aqueous acid. The levels of metal salts/ions in the final isolated product may be less than about 200 ppm. In some embodiments, the levels of metal salts/ions in the final isolated product may be less than about 100 ppm, and in some embodiments, less than about 50 ppm. In still other embodiments, the levels of metal salts/ions in the final isolated product may be less than about 5 ppm. For example, if potassium hydroxide is used as the catalyst and phosphoric acid is used to neutralize the potassium hydroxide catalyst, then the final hindered phenol alkyl ester product may contain less than about 100 ppm potassium, and in some embodiments, less than about 50 ppm potassium. Likewise, the final hindered phenol alkyl ester product may contain less than about 20 ppm phosphorous, and in some embodiments, less than about 5 ppm phosphorous.

The final water content of the reaction mix is often at least about 0.2 wt % of the total reaction mass. Advantageously, this means that very little water is used in the wash-free production process, which leaves essentially no trace of insoluble salts in the organic phase after filtration. By way of example, the water content of the final reaction mix is usually between about 0.2 to about 20 wt. % water of the reaction mass. In other embodiments, the water content of the reaction is usually between about 0.5 to about 10 wt. % water of the reaction mass, and in some cases, the water content is between about 1 to about 5 wt. % of the reaction mass.

As mentioned above, an optional promoter may be used in the Michael reaction and/or during the transesterification reaction. Promoters are often used, but not always required, to improve reaction rate, improve the reaction conversion, and reduce the amount of undesirable impurities in the product.

Typical promoters may be polar aprotic solvents. Other examples of promoters that are suitable for use with the present invention include, but are not limited to, dialkyl sulfoxides (e.g., dimethyl sulfoxide ("DMSO")), dimethyl formamide ("DMF"), dialkyl ethers (e.g., diethyl ether, diisopropyl ether), dimethyl acetamide, N,N-dialkyl acidamide, methyl ethyl ketone, methyl butyl ketone, and mixtures thereof. In addition, phase transfer catalysts such as tris(3,6-dioxaheptyl)amine, which are also called TDA-1 phase transfer agents and are sold by Rhone-Poulenc, may also be used as a promoter. Various other phase transfer catalysts and aprotic solvents may also be used. Other classes of promoters include the crown ethers such as 1,4,7,10,13-pentaoxacyclopentadecane (15-Crown-5); 1,4,7,10,13,16-hexaoxacyclooctadecane (18-Crown-6); 1,4,7,10-tetraoxacyclododecane (12-Crown-4); dibenzo-18-crown-6-dibenzyl-24-crown-8; dicyclohexano-18-crown-6; dicyclohexano-24-crown-8; and the like. Another agent suitable for the invention is sulfolane (tetramethylene sulfone).

In certain aspects of the present invention, the two-step method may incorporate a promoter in the Michael reaction and/or transesterification reaction that allows for the production of the hindered phenolic alkyl ester product in a substantially liquid form. In this embodiment, methyl acrylate is first reacted with an alkylphenol compound in the presence of a first promoter and a first catalyst to form a methyl ester intermediate compound. The intermediate compound is then reacted with an alcohol in the presence of an optional second promoter that may have the same chemical composition as the first promoter and that may have a different chemical composition than the first promoter. When the second promoter is present during the reaction of the alcohol with the methyl ester intermediate compound, the first promoter may also be used as the second promoter.

For this two-step method, the intermediate compound can also be reacted with the alcohol in the presence of the same first catalyst or a different second catalyst in order to form the hindered phenolic alkyl ester product in a substantially liquid form. The catalysts may be neutralized with any suitable aqueous acid. For this particular two-step method, the hindered phenolic alkyl ester product will remain in a liquid form, even at room temperature.

Likewise, the one-step method may incorporate a promoter during the reaction of an alkylphenol with an alkyl acrylate that allows for the production of the hindered phenolic alkyl ester product in a substantially liquid form. The catalyst for this particular one-step method may be neutralized with any suitable aqueous acid.

In some embodiments, the one-step and two-step methods of the present invention incorporate tetrahydrofuran (THF) as the promoter for the Michael reaction and/or the transesterification reaction. THF provides certain advantages over the polar aprotic solvents in the reactions of the present invention. For the two-step reaction, THF can be easily removed from the Michael reaction and then recycled during the transesterification reaction, thus making the overall process more cost effective. This allows for effective recycling of the THF promoter, the methyl acrylate in the Michael reaction, and the alcohol in the transesterification reaction.

By recycling efficiently, many of the associated manufacturing costs may be substantially reduced. This is especially true when $C_7$-$C_9$ alcohols are employed. Likewise, the one-step reaction can also utilize THF as a promoter to improve the overall efficiency because THF can more easily be removed from the alcohol.

In other embodiments of the invention, when THF is used as the promoter in the two-step method, different catalysts may be used during the Michael reaction and the transesterification reaction. Other advantages of using THF as the promoter in either or both of the Michael reaction and transesterification reaction include production of the hindered phenolic alkyl ester product as a solid or as a liquid. In addition, using THF in the one-step and two-step methods allows for neutralizing the base catalyst with any suitable aqueous acid.

The amount of promoter used according to the invention may vary over a broad range with a suitable range for the amount of promoter being between about 0.5 mole % to about 15.0 mole % of the alkylphenol reactant and, in other embodiments, being between about 1.0 mole % to about 10.0 mole % of the alkylphenol reactant. In still further embodiments, a suitable range for the amount of promoter is between about 3.0 mole % to about 7.0 mole % of the alkylphenol reactant and, in some instances, is about 5.5 mole % of the alkylphenol reactant.

The present invention also encompasses novel hindered phenolic ester compositions, and in some embodiments, the present invention encompasses any one or more of the hindered phenolic compounds made according to any of the methods described herein. For example, in one embodiment, the present invention encompasses a composition comprising the following mixture of hindered phenolic esters:

(a) 3,5-di-tert-butyl-4-hydroxyhydrocinnamic acid, $C_4$-$C_{10}$ alkyl ester, (b) pentanedioic acid, 2-[[3,5-di-tert-butyl-4-hydroxyphenyl]methyl]$C_1$-$C_{10}$ dialkyl ester, and (c) 3,5-di-tert-butyl-4-hydroxyhydrocinnamic acid, methyl ester.

In certain aspects of the invention, an optional 2,6-di-tert-butylphenol compound may also be present in the composition.

The 3,5-di-tert-butyl-4-hydroxyhydrocinnamic acid, $C_4$-$C_{10}$ alkyl ester may be present within the mixture of hindered phenolic esters in an amount that is detectable by gas chromatography and may have a gas chromatogram within the mixture of about 80.0% to about 98.0% by area, and in some embodiments, the 3,5-di-tert-butyl-4-hydroxyhydrocinnamic acid, $C_4$-$C_{10}$ alkyl ester may have a gas chromatogram within the mixture of about 90.0 to 97.0% by area. In other embodiments, the 3,5-di-tert-butyl-4-hydroxyhydrocinnamic acid, $C_4$-$C_{10}$ alkyl ester may have a gas chromatogram within the mixture of about 95.0 to 98.0% by area.

In some embodiments, the 3,5-di-tert-butyl-4-hydroxyhydrocinnamic acid, $C_4$-$C_{10}$ alkyl ester comprises at least one compound selected from the group consisting of:

3,5-di-tert-butyl-4-hydroxyhydrocinnamic acid, isooctyl ester, 3,5-di-tert-butyl-4-hydroxyhydrocinnamic acid, 2-ethylhexyl ester, 3,5-di-tert-butyl-4-hydroxyhydrocinnamic acid, n-butyl ester, and mixtures thereof.

The pentanedioic acid, 2-[[3,5-di-tert-butyl-4-hydroxyphenyl]methyl]$C_1$-$C_{10}$ dialkyl ester may be present within the mixture of hindered phenolic esters in an amount that is detectable by gas chromatography and may have a gas chromatogram within the mixture of, about 1.0% to about 20.0% by area, and in some embodiments, the pentanedioic acid, 2-[[3,5-di-tert-butyl-4-hydroxyphenyl]methyl]$C_1$-$C_{10}$ dialkyl ester may have a gas chromatogram within the mixture of about 1.5% to about 10% by area. In other embodiments, the pentanedioic acid, 2-[[3,5-di-tert-butyl-4-hydroxyphenyl]methyl]$C_1$-$C_{10}$ dialkyl ester may have a gas chromatogram within the mixture of about 1.0% to about 2.5% by area.

In certain aspects of the invention, the pentanedioic acid, 2-[[3,5-di-tert-butyl-4-hydroxyphenyl]methyl]$C_1$-$C_{10}$ dialkyl ester compound in the mixture may comprise a mixture of pentanedioic acid, 2-[[3,5-di-tert-butyl-4-hydroxyphenyl]methyl]$C_1$-$C_{10}$ alkyl esters where one alkyl ester is a $C_1$-$C_{10}$ alkyl ester and a second alkyl ester is a $C_4$-$C_{10}$ alkyl ester. For example, in one embodiment, the pentanedioic acid, 2-[[3,5-di-tert-butyl-4-hydroxyphenyl]methyl]$C_1$-$C_{10}$ alkyl ester may comprise a mixture of at least one compound selected from the group consisting of:

pentanedioic acid, 2-[[3,5-di-tert-butyl-4-hydroxyphenyl]methyl]dibutyl ester, pentanedioic acid, 2-[[3,5-di-tert-butyl-4-hydroxyphenyl]methyl]bis(2-ethylhexyl)ester, pentanedioic acid, 2-[[3,5-di-tert-butyl-4-hydroxyphenyl]methyl]diisooctyl ester, and pentanedioic acid, 2-[[3,5-di-tert-butyl-4-hydroxyphenyl]methyl]diisoheptyl ester, and at least one compound selected from the group consisting of:

pentanedioic acid, 2-[[3,5-di-tert-butyl-4-hydroxyphenyl]methyl]methyl butyl ester, pentanedioic acid, 2-[[3,5-di-tert-butyl-4-hydroxyphenyl]methyl]methyl 2-ethyl hexyl ester, pentanedioic acid, 2-[[3,5-di-tert-butyl-4-hydroxyphenyl]methyl]methyl isooctyl ester, and pentanedioic acid, 2-[[3,5-di-tert-butyl-4-hydroxyphenyl]methyl]methyl isoheptyl ester, and mixtures thereof.

The 3,5-di-tert-butyl-4-hydroxyhydrocinnamic acid, methyl ester may be present within the mixture of hindered phenolic esters in an amount that is detectable by gas chromatography and may have a gas chromatogram within the mixture of about 0.1% to about 1.0% by area, and in some embodiments, the 3,5-di-tert-butyl-4-hydroxyhydrocinnamic acid, methyl ester may have a gas chromatogram within the mixture of about 0.1% to about 5.0% by area and in some instances from about 0.5% to about 1.0% by area.

When the optional 2,6-di-tert-butylphenol compound is present within the mixture of hindered phenolic esters, it is detectable by gas chromatography and may have a gas chromatogram within the mixture of about 0.1% to about 5.0% by area and in some instances from about 0.5% to about 1.0% by area.

The compositions described herein may also include conventional amounts of other components that are commonly found in antioxidant compositions and in the combination of lubricating oils and antioxidant compositions. For instance, corrosion inhibitors, extreme pressure agents, and antiwear agents may be included and are exemplified, but are not limited to, dithiophosphoric esters, chlorinated aliphatic hydrocarbons, boron-containing compounds including borate esters, and molybdenum compounds.

Viscosity index improvers may be included and are exemplified, but are not limited to, polyisobutenes, polymethyacrylate acid esters, polyacrylate acid esters, diene polymers, polyalkyl styrenes, alkenyl aryl conjugated diene copolymers, polyolefins and multifunctional viscosity improvers.

Pour point depressants are a particularly useful type of additive, and are often included in the compositions described herein. Such depressants include, but are not limited to, polymethacrylates, styrene-based polymers, crosslinked alkyl phenols, or alkyl naphthalenes.

Foam inhibitors used to reduce or prevent the formation of stable foam may also be included with compositions described herein. Suitable foam inhibitors include, but are not limited to, silicones or organic polymers.

Dispersants may also be included and are exemplified, but are not limited to, Mannich bases, high molecular weight esters, hydrocarbon-based dispersants, carboxylic dispersants (e.g. succinic-based dispersants), and mixtures thereof.

Additional supplemental antioxidants may also be included, such as aromatic amines (alkylated diphenylamines), other types of hindered phenols, sulfurized phosphorous compounds and molybdenum containing antioxidants, and mixtures thereof.

Other compounds that may be included with the compositions described herein are detergents (e.g. metal overbased salts of organic acids such as zinc dialkyldithiophosphate), rust inhibitors, friction modifiers, and mixtures thereof. These and other additives which may be used in combination with the compositions described herein are illustrated in greater detail in U.S. Pat. No. 4,582,618 to Davis, which is incorporated herein in its entirety by reference thereto.

Therefore, in certain embodiments, the present invention provides a composition comprising any one or more of the mixtures of hindered phenolic esters described previously in combination with at least one compound selected from the group consisting of a lubricant oil, a dispersant, a detergent, an antiwear additive, a supplemental antioxidant, zinc dialkyldithiophosphate, an alkylated diphenylamine, a viscosity index improver, a pour point depressant, a corrosion inhibitor, a rust inhibitor, a foam inhibitor, a supplemental friction modifier, and mixtures thereof.

In other embodiments, the present invention provides a composition comprising a detergent, a dispersant, a zinc dialkyldithiophosphate and at least the following hindered phenolic esters:

(a) 3,5-di-tert-butyl-4-hydroxyhydrocinnamic acid, $C_4$-$C_{10}$ alkyl ester, (b) pentanedioic acid, 2-[[3,5-di-tert-butyl-4-hydroxyphenyl]methyl]$C_1$-$C_{10}$ dialkyl ester, and (c) 3,5-di-tert-butyl-4-hydroxyhydrocinnamic acid, methyl ester.

In still other embodiments, the present invention provides a composition comprising a corrosion inhibitor, a rust inhibitor, an alkylated diphenylamine and at least the following hindered phenolic esters:

(a) 3,5-di-tert-butyl-4-hydroxyhydrocinnamic acid, $C_4$-$C_{10}$ alkyl ester, (b) pentanedioic acid, 2-[[3,5-di-tert-butyl-4-hydroxyphenyl]methyl]$C_1$-$C_{10}$ dialkyl ester, and (c) 3,5-di-tert-butyl-4-hydroxyhydrocinnamic acid, methyl ester.

The present invention also provides compositions containing any of the hindered phenolic compounds described herein that are also in combination with organic materials, which are sensitive to oxidative and/or thermal degradation such as, for example, a polymer, fuel, feed oil, or lubricant fluid. Specific materials that can be stabilized with the hindered phenolic compounds made according to the methods described herein include, but are not limited to, lubricating fluids of the aliphatic ester type (e.g., di-(2-ethylhexyl)-azelate, pentaerythritol tetracaproate), passenger car engine oils, heavy duty diesel engine oils, railroad oils, natural gas engine oils, turbine oils, rust oils, oxidation oils, slideway oils, hydraulic oils, industrial oils, automotive gear oils, automatic transmission fluids and manual transmission fluids, tractor fluids, universal tractor fluids and hydraulic fluids, power steering fluids, gear lubricants, industrial oils, pump oils, and mixtures thereof, and any other lubricating oil compositions that may benefit from the incorporation therein of the hindered phenolic compounds made according to the methods of the present invention.

The compositions of the present invention may also be suitably incorporated into synthetic base oils such as alkyl esters of dicarboxylic acids, polyglycols and alcohols, poly-alphaolefins, alkyl benzenes, organic esters of phosphoric acids, polysilicone oils, etc. Natural base oils include mineral lubricating oils which may vary widely as to their crude source, e.g., whether paraffinic, naphthenic, mixed, paraffinic-naphthenic, and the like as well as to their formation, e.g., distillation range, straight run or cracked, hydrorefined, solvent extracted and the like.

The hindered phenolic compounds made according to the methods of the present invention are especially useful in crankcase lubricants where they act as antioxidants and reduce sludge formation.

Other materials which can be stabilized with the hindered phenolic compounds made according to the methods described herein, include, but are not limited to, synthetic organic polymeric substances such as vinyl resins formed from the polymerization of vinyl halides or from the copolymerization of vinyl halides with unsaturated polymerizable compounds, e.g., vinyl esters, alpha, beta-unsaturated acids, alpha, beta.-unsaturated esters, alpha, beta unsaturated ketones, alpha, beta-unsaturated aldehydes and unsaturated hydrocarbons such as butadienes and styrene; poly-alpha-olefins such as polyethylene, polypropylene, polybutylene, polyisoprene, including copolymers of poly-alpha-olefins; polyurethanes prepared from polyols such as propylene glycol or ethylene glycol and organic polyisocyanates; polyamides such as polyhexamethylene adipamide; polyesters such as polymethylene terephthalates; polycarbonates; polyacetals; polystyrene, polyethylene oxide; and copolymers such as those of high impact polystyrene containing copolymers of butadiene and styrene and those formed by the copolymerization of acrylonitrile, butadiene and/or styrene; animal and vegetable derived oils, e.g., linseed oil, fat, tallow, lard, peanut oil, cod liver oil, castor oil, palm oil, corn oil, cotton seed oil; hydrocarbon materials such as gasoline, both natural and synthetic, diesel oil, mineral oil, fuel oil, drying oil, cutting fluids, waxes; fatty acids such as soaps; hydrocarbon resins; unsaturated polyester resins derived from copolyesters of saturated and unsaturated dicarboxylic acids with polyvalent alcohols, and vinyl compounds as cross-linking agents; cross-linkable acrylic resins; alkyl resins, polyester resins and acrylate resins; cross-linked epoxy resins; natural polymers, such as cellulose, natural rubber, gelatine and the polymer-homologously chemically modified derivatives thereof, such as cellulose acetates, propionates and butyrates, and the cellulose ethers, such as methylcellulose; colophonium resins and derivatives; natural and synthetic organic substances that are pure monomeric compounds or mixtures thereof, for example mineral oils, animal or vegetable fats, oils and waxes, or oils, waxes and fats based on synthetic esters, e.g., phthalates, adipates, phosphates or trimellitates); aqueous emulsions of natural or synthetic rubbers, e.g. natural latex rubber or latices of carboxylated styrene-butadiene copolymers; and fuels, e.g., jet fuels, gasolines, heating oils, gasohol, and diesel fuels.

The hindered phenolic antioxidants of the invention may be incorporated into the aforementioned organic materials by mixing in the antioxidants of the invention and, where applicable, other additives such as the ones described below, by methods customary in the art. For example, the hindered phenolic antioxidants made according to the methods of the present invention can be added to the materials to be stabilized in the form of a master batch which contains the antioxidant in a liquid or solid form.

Advantageously, the hindered phenolic compounds of the present invention can be incorporated as an emulsion or dispersion (e.g., to latices or emulsion polymers), as a dry mixture during the mixing of additional components or polymer mixtures, as a direct addition into the processing apparatus (e.g., extruder, kneader, etc.), or as a solution or melt. In one embodiment, the hindered phenolic compound is added to the materials to be stabilized in a substantially liquid form.

The hindered phenol compounds made according to the methods described herein are added to compositions in need of stabilizing in any amount. Various antioxidant-effective amounts of adding the inventive compounds can range from about 0.001 wt. % to about 90.0 wt. %, from about 0.01 to about 25.0 wt. %, from about 0.10 to about 2.0 wt. %, and from about 0.2 to about 1.5 wt. %, based on the total weight of the composition. Generally, the hindered phenol compounds may also be added to compositions in need of stabilizing at about 1.0 wt. %, based on the total weight of the composition.

For example, in certain aspects of the invention, a composition is provided that comprises a lubricating oil, about 1.0% to about 7.5% by weight of a detergent, about 1.0% to about 7.5% by weight of a dispersant, about 0.5% to about 1.5% by weight of zinc dialkyldithiophosphate, and about 0.1% to about 2.0% by weight of any of the mixtures of hindered phenolic esters described previously.

In other embodiments, the present invention provides a composition comprising a lubricating oil, about 0.01% to about 0.5% by weight of a corrosion inhibitor, about 0.01% to about 0.5% by weight of a rust inhibitor, about 0.1% to about 1.0% by weight of an alkylated diphenylamine, and about 0.1% to about 1.0% by weight of any of the mixtures of hindered phenolic esters described previously.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLE 1

This example demonstrates a two-step method for the production of 3,5-di-tert-butyl-4-hydroxyhydrocinnamic acid, isooctyl ester, which is suitable for use as an antioxidant.

Step 1: Michael Reaction.

A 1-liter round bottom Pyrex flask equipped with a magnetic stir bar, temperature probe, heating mantle, and total condenser for distillate removal was used. The flask was initially charged with 350.7 g of molten 2,6-di-tert-butylphenol ("2,6-DTBP", 1.70 mol) at 40 to 50° C., 2.42 g of potassium hydroxide (KOH) pellet, and 14.7 g of DMSO. The pressure was then reduced to 15 mm Hg and the temperature was increased from 40° C. to 115° C. over 70 minutes to remove the water by-product. The resulting white slurry was then cooled to 110° C.

A water-cooled total reflux condenser and a 250-ml addition funnel containing 155.6 g of methyl acrylate were installed to the reactor. The methyl acrylate ("MA") was added dropwise over 30 minutes, during which the temperature of the reactor was allowed to rise from 110° C. to 129° C. The reactor was heated further to 135° C. in 6 minutes, then cooled to 110° C. and held at 110° C. for 170 minutes. The red clear solution was analyzed by Gas Chromatography ("GC") and found to contain 1.2 area % 2,6-di-tert-butylphenol and 96.0 area % 3,5-di-tert-butyl-4-hydroxyhydrocinnamic acid, methyl ester. The pressure was then reduced to 20 mm Hg, and the excess methyl acrylate was stripped at 110° C. The intermediate was analyzed by GC and found to contain 93.9 wt. % 3,5-di-tert-butyl-4-hydroxyhydrocinnamic acid, methyl ester and 0.67 wt. % 2,6-DTBP. A 21.5 g portion of the 3,5-di-tert-butyl-4-hydroxyhydrocinnamic acid, methyl ester intermediate was used for physical property measurements.

Step 2: Transesterification Reaction.

A Vigreux column equipped with an air-cooled partial condenser and a −15° C. glycol-cooled total condenser was installed to the reactor. The remaining 3,5-di-tert-butyl-4-hydroxyhydrocinnamic acid, methyl ester intermediate (~1.63 mol) was added with 225.8 g of isooctanol. The mixture was heated slowly from 65° C. to 176° C. over 3.2 hours at a reduced pressure of 300 mm Hg initially to 60 mm Hg at end, during which approximately 65 ml of methanol distillate was collected in the trap receiver. The resulting reaction mass was found (by GC) to contain 2.7 area % isooctanol, 0.83 area % 2,6-DTBP, 0.81 area % 3,5-di-tert-butyl-4-hydroxyhydrocinnamic acid, methyl ester, and 94.8 area % 3,5-di-tert-butyl-4-hydroxyhydrocinnamic acid, isooctyl ester.

After removing the column and the air-cooled partial condenser, the excess isooctanol was stripped off at 5 mm Hg and 185° C. The resulting 3,5-di-tert-butyl-4-hydroxyhydrocinnamic acid, isooctyl ester crude product was found (by GC) to contain 0.35 area % isooctanol, 0.30 area % 2,6-DTBP, 0.68 area % 3,5-di-tert-butyl-4-hydroxyhydrocinnamic acid, methyl ester, and 97.34 area % 3,5-di-tert-butyl-4-hydroxyhydrocinnamic acid, isooctyl ester.

Step 3: Neutralization of the Potassium Catalyst with Phosphoric Acid.

7.156 g of 42.51 wt. % $H_3PO_4$ (31.0 mmol) in water and 31.7 g of additional water were added at 86° C. to the above 3,5-di-tert-butyl-4-hydroxyhydrocinnamic acid, isooctyl ester solution, which contained 41.4 mmol of K catalyst. The mixture was kept at 86° C. to 92° C. for 38 minutes at atmospheric pressure. The temperature was then slowly raised from 88° C. to 125° C. and the pressure was reduced gradually to 20 mm Hg over 30 minutes to strip off the water (34.0 g collected). After cooling to 80° C., the precipitated solids were filtered in less than two minutes using a 9-cm Whatman-541 filter paper. The analytical results of the filtrate are given in Table 1.

EXAMPLE 2

This example demonstrates another two-step method for the production of 3,5-di-tert-butyl-4-hydroxyhydrocinnamic acid, isooctyl ester, which is suitable for use as an antioxidant.

Step 1: Michael Reaction.

A 12-liter round bottom Pyrex flask equipped with an overhead agitator, temperature probe, heating mantle, and a reflux condenser in series of a total condenser for distillate removal were used. The flask was initially charged with 4126.4 g of molten 2,6-DTBP (20.0 mol) at 40 to 50° C., 28.1 g of KOH pellet (0.50 mol), and 85.9 g of DMSO (1.1 mol). The pressure was then reduced to 20 mm Hg and the temperature was increased from 40° C. to 126° C. over 76 minutes to remove the water by-product. The resulting white slurry was then cooled to 110° C.

Cooling water was then put to the jacket of the reflux condenser and 995.2 g of methyl acrylate (11.56 mol) was then added dropwise from a 1000-ml funnel to the reactor over 37 minutes, during which time the reactor temperature was allowed to rise from 110° C. to 117° C. A stream of nitrogen was injected between the heating mantle and the reactor wall to remove the heat. The dropping funnel was immediately recharged with an additional 847.4 g of methyl acrylate (9.84 mol), which was added dropwise to the reactor over 39 minutes, while the reactor temperature was allowed to increase to 130° C. The reactor temperature was then brought to 140° C. over 10 minutes before cooling to 110° C. over 25 minutes. After a 110 minute hold at 110° C., the reaction mass was found to contain 1.58 area % 2,6-DTBP and 96.7 area % 3,5-di-tert-butyl-4-hydroxyhydrocinnamic acid, methyl ester. The reaction mass was held for 30 minutes longer at 110° C., before the excess methyl acrylate was stripped off at 110° C. and 20 mm Hg. The resulting 3,5-di-tert-butyl-4-hydroxyhydrocinnamic acid, methyl ester was analyzed by GC and found to contain 0.47 wt. % 2,6-DTBP and 94.85 wt. % 3,5-di-tert-butyl-4-hydroxyhydrocinnamic acid, methyl ester, and 1.75 area % diesters.

Step 2: Transesterification Reaction.

The above-mentioned reflux condenser was packed with 4.5" S.S. Propak®, which improved the separation of MeOH from the isooctanol and DMSO. The 3,5-di-tert-butyl-4-hydroxyhydrocinnamic acid, methyl ester intermediate was added with 2,789.6 g of Isooctanol (21.42 mol). The mixture was heated slowly from 71° C. to 166° C. over 4.2 hours at 25 mm Hg, during which 661 g of methanol was collected in the trap receiver. After removing the reflux condenser, the excess isooctanol and DMSO (206.3 g collected) were stripped off at 5 mm Hg and 185° C.

Step 3: Neutralization of the potassium catalyst with phosphoric acid.

132.2 g of water and 42.8 g of 85.8 wt. % $H_3PO_4$ (0.375 mol) in water was added at 70° C. to the above 3,5-di-tert-butyl-4-hydroxyhydrocinnamic acid, isooctyl ester solution, which contained 0.5 mol of K. The reactor temperature was kept at 70° C. for one hour, increased to 100° C. over 43 minutes, and held at 100° C. for 30 minutes at nitrogen atmospheric pressure. Then, the reactor temperature was brought up from 100° C. to 125° C. over 62 minutes, while the pressure was reduced gradually to 20 mm Hg to strip off the water, during which solid precipitations were noted. After releasing the vacuum, the slurry was filtered via a medium fritted glass funnel. The analyses of the filtrate are given in Table 1. Analysis of the residual metal salts/ions in the final product was performed by Inductively Coupled Plasma Atomic Emission Spectroscopy ("ICP").

TABLE 1

| Two-Step Method Analysis | | |
|---|---|---|
| | Example 1 | Example 2 |
| Michael Rxn. | | |
| 2,6-DTBP (mol) | 1.70 | 20.0 |
| KOH/2,6-DTBP (mol/mol) | 0.025 | 0.025 |
| DMSO/2,6-DTBP (mol/mol) | 0.11 | 0.055 |
| MA/2,6-DTBP (mol/mol) | 1.06 | 1.070 |
| Temp (° C.) | 110-135 | 110-140 |
| Rxn Time (hr) | 3.7 | 4.2 |
| Tranesterification Rxn. | | |
| isooctanol/2,6-DTBP (mol/mol) | 1.06 | 1.07 |
| Final Temp (° C.) | 176 | 166 |
| Final Pres. (mm Hg) | 60 | 25 |
| Rxn Time (hr) | 3.2 | 4.2 |
| Neutralization | | |
| $H_3PO_4$/K (mol/mol) | 0.75 | 0.75 |
| $H_3PO_4$ conc. (wt. %) | 7.8 | 21.0 |
| Neutralization Condition | 38 minutes at 86-92° C. | 60 mins. at 70° C. 43 mins. at 70-100° C. 30 mins. at 100° C. |
| Final Product Analyses | | |
| 2,6-DTBP (wt. %), GC | 0.31 | 0.32 |
| 3,5-di-tert-butyl-4-hydroxyhydrocinnamic acid, methyl ester (wt. %), GC | 0.55 | 1.08 |

TABLE 1-continued

| Two-Step Method Analysis | | |
|---|---|---|
| | Example 1 | Example 2 |
| 3,5-di-tert-butyl-4-hydroxyhydrocinnamic acid, isooctyl ester (%), GC | 96.8 | 96.05 |
| Isooctanol (wt. %), GC | 0.41 | 0.65 |
| Diesters (%), GC | 1.74 | 1.70 |
| Others (%), GC | 0.19 | 0.20 |
| K (ppm), ICP | 18.8 | 51 |
| P (ppm), ICP | 2.0 | 1 |

EXAMPLE 3

This example illustrates how an aqueous acid such as phosphoric acid can be used, in a process without the need to employ water washings, to produce a hindered phenolic ester product (2,6-di-tert-butyl-4-hydroxyhydrocinnamic acid, butyl ester) that contains very low levels of potassium catalyst residues.

For this example, 206.4 g of 2,6-DTBP (1.00 mol), 50.8 g toluene, and 1.17 g KOH pellets (0.020 mol, 2.0 mol %) are charged into a 1 liter flask equipped with mechanical stirrer, connected to a Dean-Stark trap and under $N_2$ atmosphere. The mixture is heated to 140° C. to remove water as a toluene azeotrope. A white slurry was obtained and 14.1 g of toluene was collected. Butyl acrylate (130.2 g, 1.015 mol) was then added in one portion over two minutes to the white slurry. The Dean-Stark trap was removed and replaced by a cooling condenser. The resulting mixture was heated for 5 hours at 140° C., during which time 14 g toluene was collected and the resulting orange reaction mixture became a totally clear solution. GC analysis showed approximately 97% conversion of the 2,6-di-tert-butylphenol.

The mixture was allowed to cool down to 113° C. before acidifying with 10 g of 17 wt. % $H_3PO_4$ (0.017 mol, approximately 87 mol % of theoretical potassium catalyst present) and mixed for approximately 1 hour. The excess toluene and water were then removed under reduced pressure at a temperature between room temperature and 140° C. (pressure down to 4.5 torr). The resulting light yellow oil was filtered at about 120° C. over a celite bed (5 g) to remove potassium salts. Approximately 320 grams of product was obtained.

GC wt. % analysis showed 95.4% 2,6-di-tert-butyl-4-hydroxyhydrocinnamic acid, butyl ester and 2.8% 2,6-DTBP. (ICP data: 2.3 ppm K and <1 ppm P. Density: 0.9817 g/ml (@ 25° C.); Kinematic Viscosity: 65.9 (@ 40° C.)).

In this Example, the theoretical amount of potassium, if none were removed from the product, is approximately 2540 ppm. Therefore, greater than 99.9% of the potassium is removed according to method of this Example. Typically, 96.0 to 100.0% of the potassium catalyst may be removed by the method of this Example.

These results suggest that the wash-free neutralization of potassium counterions is an efficient tool and a viable alternative to aqueous wash and phase separation. Table 2 below summarizes the relationship between mol % added phosphoric acid (as a mol % of original KOH used) and the trace potassium and phosphorus in parts per million for various final phenolic alkyl ester products at varying amounts of KOH catalyst and aqueous phosphoric acid.

TABLE 2

The Efficiency of the Wash-Free Neutralization in Removing the Catalyst

| Phenolic Alkyl Ester Product | Original KOH (mmol) | H₃PO₄ (mol %) | Potassium (ppm) | Phosphorous (ppm) |
|---|---|---|---|---|
| butyl ester | 9.6 | 99 | <1 | <3 |
| butyl ester | 10 | 87 | 5.1 | <5 |
| butyl ester | 20 | 87 | 2.3 | <1 |
| butyl ester | 37 | 85 | 100 | 18.8 |
| ethylhexyl ester | 40 | 87 | 0.073 | <0.14 |
| ethylhexyl ester | 19 | 91 | 0.9 | <0.5 |
| ethylhexyl ester | 24 | 76 | 142 | 7.6 |
| ethylhexyl ester | 39 | 88 | <0.1 | <2 |

EXAMPLE 4

This example illustrates the improvement obtained in producing hindered phenolic esters when a polar promoter is employed during the Michael reaction. As described in U.S. Pat. No. 4,085,132, hindered phenolic esters with low conversions and low purities may be produced. Furthermore, as known in the art, the addition of a polar promoter significantly improves the conversion and yield of the hindered phenolic ester to the point where the process can be used to produce liquid products or eliminate crystallization or distillation.

Reaction 1: The influence of having a polar promoter in the Michael reaction.

The reaction of butyl acrylate with 2,6-DTBP at 120° C. was monitored as a function of time in the presence of a DMSO promoter and with 2 mol % KOH as the alkaline catalyst. The GC results are shown in Table 2 below.

Reaction 2: The influence of not having a polar promoter in the Michael reaction.

The reaction of butyl acrylate with 2,6-DTBP at 120° C. was monitored as a function of time using 2 mol % KOH as the alkaline catalyst. The GC results are shown in Table 3 below.

TABLE 3

Effect of DMSO on the Rate of Michael Addition.

| | Reaction Time (hours) | GC area % 2,6-DTBP | GC area % Product |
|---|---|---|---|
| No DMSO | 4 | 34.5 | 64.1 |
| | 9 | 9.4 | 89.4 |
| | 12 | 6.4 | 92.8 |
| | 15 | 5.8 | 93.7 |
| Plus 6 mole % DMSO | 4 | 2.1 | 95.3 |
| | 9 | 0.62 | 97.1 |

Without the presence of a polar promoter, such as DMSO, a purity of only 89.4% was achieved after 9 hours. After the reaction was conducted for 15 hours, the purity only improved to 93.7%. However, for purposes of the present invention, a 15-hour reaction time is not cost effective or practical. For a solid product, crystallization can improve the purity of the 89.4% reaction mixture. However, this would result in a significant yield loss. For a liquid product, the only purification option is a costly and time consuming distillation step. For the hindered phenolic compounds of the present invention, it has been found that improved conversion and purity may be achieved, while avoiding an expensive and time consuming distillation procedure.

In the presence of a polar promoter, such as DMSO, a purity of 97.1% is achieved after 9 hours. In fact, a purity of 95.1% is achieved after only 4 hours when DMSO is present. This process, containing a DMSO promoter, now eliminates the need for crystallization (in the case of solids) or distillation (in the case of liquids). The purity of this product is such that it can be used in most lubricant applications.

EXAMPLE 5

This example demonstrates a one-step method for the production of 3,5-di-tert-butyl-4-hydroxyhydrocinnamic acid, 2-ethylhexyl ester, which is suitable for use as an antioxidant.

More than a half dozen runs were carried out to identify the ideal reaction conditions for obtaining high purity ester. By using KOH as the catalyst, it was concluded that the presence of DMSO promoter roughly doubles the reaction rate under identical reaction conditions. Water is typically removed as a toluene azeotrope prior to the Michael addition step. The flask is heated by means of a heating mantle. The examples where 3,5-di-tert-butyl-4-hydroxyhydrocinnamic acid, 2-ethylhexyl ester was obtained in 95% or greater purity are detailed below.

Single step method using 2,6-di-tert-butylphenol and 2-ethylhexyl acrylate ("2-EHA").

Into a 2-liter round bottom flask equipped with magnetic stirring bar and connected to Dean-Stark trap under nitrogen atmosphere, the following were charged:

412.8 g 2,6-DTBP (2.00 mol)

50 g toluene 2.20 g KOH pellets (39.2 mmol, 1.96 mol %)

9.3 g (~8 mL) DMSO promoter (119 mmol, 5.9 mol %)

The colorless slurry was heated to 150° C. to remove the water/toluene azeotrope. A white slurry was obtained and 11.9 g of hazy toluene was collected in the trap. The Dean-Stark trap was removed and a cooling condenser was connected to the reactor and the reaction temperature was reset to 140° C. The 2-ethylhexylacrylate (2-EHA, 402 g, 2.18 mol) was then added over 30 minutes. The resulting mixture was heated for a total of 6 hours at 140° C., during which time the temperature initially rose to 149° C. before subsiding back to 140° C. GC analysis of the clear red orange reaction mixture showed >98% 2,6-di-tert-butylphenol converted to product(s).

Neutralization and Solvent Removal.

The resulting red orange reaction solution (containing the catalyst residue) was neutralized at 100° C. by addition of 20 g of 17.0 wt. % (34.7 mmol acid, ~88% of theoretical KOH catalyst) phosphoric acid. The acid solution was prepared by mixing 4.0 g of 85% phosphoric acid and 16.0 g water. Mixing continued and the reaction mixture was allowed to cool down to room temperature. The excess toluene and water were then removed under reduced pressure between room temperature and 150° C. (down to 1.2 torr). The resulting oil was filtered while hot (140° C.) over a celite bed (5 g) to remove potassium salts. A clear light yellow product (Gardner color 4.7) was obtained in near quantitative yield.

(GC Analysis: 94.84% 3,5-di-tert-butyl-4-hydroxyhydrocinnamic acid, 2-ethylhexyl ester, 0.69 wt. % 2,6-di-tert-butylphenol, and 3.27% diesters. ICP Data: <2 ppm K, and <0.1 ppm P.)

EXAMPLE 6

This example demonstrates a two-step method for the production of 3,5-di-tert-butyl-4-hydroxyhydrocinnamic acid, 2-ethylhexyl ester, which is suitable for use as an antioxidant.

Step 1: Preparation of 3,5-di-tert-butyl-4-hydroxyhydrocinnamic acid, methyl ester.

Into a 1-liter round bottom flask equipped with magnetic stirring bar and connected to a Dean-Stark trap and cooling condenser under $N_2$ atmosphere, the following were charged:
206.3 g 2,6-DTBP (1.00 mol)
31.6 g toluene
1.33 g KOH pellets (23.7 mmol, 2.37 mol %)
4.71 g (~4 mL) DMSO promoter (60 mmol, 6.0 mol %)

The reaction was heated to 140° C. to remove the water/toluene azeotrope. A white slurry was obtained and 7.2 g hazy toluene was collected in the trap. The Dean-Stark trap was removed and a cooling condenser was connected to the reactor. The heating was reset to 120° C. Vigorous condensation was observed and 99.1 g (1.15 mol) of methyl acrylate was added over a 45-minute period. After three hours of heating at 120° C., the 2,6-di-tert-butylphenol conversion was about 98.5% complete.

Step 2: Transesterification of 3,5-di-tert-butyl-4-hydroxyhydrocinnamic acid, methyl ester and Conversion to 3,5-di-tert-butyl-4-hydroxyhydrocinnamic acid, 2-ethylhexyl ester.

The excess MA was not removed. Heating was reset to 155° C. for the transesterification and MeOH removal step. 2-Ethylhexanol (155.2 g, 1.19 mol) was charged and the reaction was heated for 4 hours with vigorous condensation while continuously purging with gentle nitrogen stream.

Neutralization and Solvent Removal.

The resulting reaction mixture was neutralized at 140° C. by addition of 10.0 g of 17 wt % (17 mmol, ~73% of theoretical KOH catalyst) phosphoric acid. The acid solution was prepared by mixing 2.0 g of 85% phosphoric acid and 8.0 g water. After mixing for 1 hour, the red solution turned yellow. The excess toluene and water were then removed under gradually reduced pressure at a temperature between 40° C. and 150° C. (down to ~1 torr). The resulting oil was filtered at about 140° C. over a celite bed (5 g) to obtain 380 g (97.4% recovery) of yellow oil.

(GC Analysis: 95.55 wt. % 3,5-di-tert-butyl-4-hydroxyhydrocinnamic acid, 2-ethylhexyl ester, 0.40 wt. % 2,6-di-tert-butylphenol, 0.54 wt. % 3,5-di-tert-butyl-4-hydroxyhydrocinnamic acid, methyl ester, and 1.89% diesters.)

EXAMPLE 7

This example demonstrates a two-step method for the production of 3,5-di-tert-butyl-4-hydroxyhydrocinnamic acid, isooctyl ester using tetrahydrofuran as a promoter.

Step 1: Preparation of 3,5-di-tert-butyl-4-hydroxyhydrocinnamic acid, methyl ester.

A 1-liter round bottom Pyrex flask equipped with a magnetic stir bar, thermal probe, heating mantle, water-cooled total reflux condenser, and 250-ml addition funnel were used. The flask was initially charged with 309.3 g of molten 2,6-DTBP (1.50 mol) at 40-50° C., 4.21 g of potassium tert-butoxide (t-BuOK), and 16.82 g of tetrahydrofuran (THF) to form a slurry. The slurry was heated to 110° C. and 142.0 g of methyl acrylate was added dropwise from the addition funnel over 98 minutes while the reactor was maintained at 110-120° C. After holding at 120° C. for 3.6 additional hours, the red clear reaction mass was found (by GC) to contain 0.46 area % 2,6-DTBP and 98.5 area % 3,5-di-tert-butyl-4-hydroxyhydrocinnamic acid, methyl ester. The pressure was then reduced to 20 mm Hg to strip off the THF and excess methyl acrylate. The methyl ester intermediate contained 96.3 wt. % 3,5-di-tert-butyl-4-hydroxyhydrocinnamic acid, methyl ester, 0.11 wt. % 2,6-DTBP, 0.04 wt % methyl acrylate, and 0.38 wt. % THF.

Step 2: Transesterification of 3,5-di-tert-butyl-4-hydroxyhydrocinnamic acid, methyl ester and Conversion to 3,5-di-tert-butyl-4-hydroxyhydrocinnamic acid, isooctyl ester.

A Vigreux column equipped with a water-cooled air-cooled partial condenser and a −15° C. glycol-cooled total condenser was installed to the reactor. The above methyl ester intermediate was added with 200.4 g of Exxal-8® isooctanol (1.539 mol). The mixture was heated slowly from 43° C. to 155° C. at reduced pressure of 300 down to 50 mm Hg over 82 minutes. Approximately 55 ml of methanol distillate was collected. Then 6 ml of toluene was added dropwise over 50 minutes to the reactor, which was kept at 155° C. and 25-50 mm Hg. The toluene was used as a chaser to strip off the methanol byproduct from the reaction mass to drive the reaction to completion. At the end of the toluene feed, the reaction mass was found (by GC) containing 1.8 area % isooctanol, 0.19 area % 2,6-DTBP, 4.89 area % 3,5-di-tert-butyl-4-hydroxyhydrocinnamic acid, methyl ester, and 92.3 area % 3,5-di-tert-butyl-4-hydroxyhydrocinnamic acid, isooctyl ester, indicating incompletion of the reaction of methyl ester to isooctyl ester. An additional 11.1 g of Exxal-8® isooctanol (0.085 mol) was charged to the reactor. Then 17 ml of toluene was added dropwise over 83 minutes, while keeping the reactor at 155° C. and 30 mm Hg. The resulting product was analyzed by GC and found to contain 1.65 area % isooctanol, 0.15 area % 2,6-DTBP, 1.12 area % 3,5-di-tert-butyl-4-hydroxyhydrocinnamic acid, methyl ester, and 96.6 area % 3,5-di-tert-butyl-4-hydroxyhydrocinnamic acid, isooctyl ester.

After removing the column and the air-cooled partial condenser, an additional 25 ml of toluene was added as a chaser to strip off the excess isooctanol at 20 mm Hg and 150-155° C. The resulting product was found (by GC) to contain 1.3 area % isooctanol, 0.2 area % 2,6-DTBP, 1.08 area % 3,5-di-tert-butyl-4-hydroxyhydrocinnamic acid, methyl ester, and 97.1 area % 3,5-di-tert-butyl-4-hydroxyhydrocinnamic acid, isooctyl ester.

Neutralization and Solvent Removal.

The resulting product was then added to 2.25 g of acetic acid the product was at a temperature of 102-110° C. in order to neutralize the potassium catalyst. The mixture turned to yellow and became cloudy. After adding 10.3 g of water, the mixture was then heated to 123° C. and the pressure was reduced to 20 mm Hg to strip off the water, THF, and unreacted acetic acid. The resulting mixture was hazy, but solid precipitations were not observed, indicating that the potassium acetate was not precipitated out as easily as the potassium phosphate salts.

Additional acetic acid (1.55 g) was added and then the product was washed twice with water (182 g and 177 g) at 80-96° C. A clear interface was noted after approximately 7 to 9 minutes, although the organic product layer was cloudy. The aqueous layers were discarded. The organic layer was further dried by vacuum stripping the mixture at 20 mm Hg and at 120° C. The 3,5-di-tert-butyl-4-hydroxyhydrocinnamic acid, isooctyl ester product weighed 587 grams.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. For example, while methods for the production of a hindered phenolic alkyl ester compound and compositions made according to those methods have been exemplified, other uses are contemplated. Therefore, the spirit and scope of the appended claims should not be limited to the description of the preferred versions contained therein.

What is claimed is:

1. A method for the production of a sterically hindered phenolic alkyl ester compound, which method comprises:
   a) reacting methyl acrylate with a sterically hindered alkylphenol compound in the presence of a first catalyst to form a methyl ester intermediate compound,
   b) reacting an alcohol having at least 2 carbon atoms with the methyl ester intermediate compound in the presence of a second catalyst to form the sterically hindered phenolic alkyl ester compound,
   c) forming a precipitated phosphate salt by steps consisting essentially of
      i) neutralizing any catalyst residue with an aqueous phosphoric acid, and
      ii) removing water to form a precipitated phosphate salt, and
   d) separating the precipitated phosphate salt from the sterically hindered phenolic alkyl ester compound,
wherein said first catalyst and said second catalyst as charged to the reactor comprise at least one compound selected from the group consisting of alkali metal hydroxides, alkali metal alkoxides, and mixtures thereof.

2. The method according to claim 1, wherein the first catalyst is also used as the second catalyst during the reaction of the alcohol with the methyl ester intermediate compound.

3. The method according to claim 1, wherein the first and second catalysts comprise at least one compound selected from the group consisting of sodium alkoxides and potassium alkoxides.

4. The method according to claim 1, wherein the first and second catalysts comprise at least one compound selected from the group consisting of sodium hydroxide and potassium hydroxide.

5. The method according to claim 1 wherein filtration is used to separate the precipitated phosphate salt from the sterically hindered phenolic alkyl ester compound.

6. The method according to claim 1, wherein the sterically hindered phenolic alkyl ester compound is formed in a liquid form.

7. The method according to claim 1, wherein the alkylphenol compound is 2,6-di-tert-butylphenol.

8. The method according to claim 1, wherein the sterically hindered phenolic alkyl ester formed is a 3,5-di-tert-butyl-4-hydroxyhydrocinnamic acid, alkyl ester.

9. The method according to claim 1, wherein the molar ratio of methyl acrylate to alkylphenol is at least 1:1.

10. The method according to claim 1, wherein a molar excess of methyl acrylate is employed so that the molar ratio of methyl acrylate to alkylphenol is greater than 1:1.

11. The method according to claim 1, wherein a molar excess of methyl acrylate is employed so that the molar ratio of methyl acrylate to alkylphenol is between about 1.05:1 to about 1.30:1.

12. The method according to claim 1, wherein a molar excess of alkylphenol is employed so that the molar ratio of alkylphenol to methyl acrylate is greater than 1:1.

13. The method according to claim 1, wherein a molar excess of alkylphenol is employed so that the molar ratio of alkylphenol to methyl acrylate is between about 1.05:1 to about 1.30:1.

14. The method according to claim 1, wherein the phosphoric acid comprises at least one compound selected from the group consisting of orthophosphoric acid ($H_3PO_4$), pyrophosphoric acid ($H_4P_2O_7$), and metaphosphoric acid ($HPO_3$).

15. The method according to claim 1, wherein the molar equivalent of aqueous phosphoric acid used is between about 10% and 200% of the total amount of catalysts used.

16. The method according to claim 1, wherein the molar equivalent of aqueous phosphoric acid used is between about 33% and 100% of the total amount of catalysts used.

17. The method according to claim 1, wherein the alcohol is a high molecular weight alcohol.

18. The method according to claim 1, wherein the methyl acrylate is reacted with the alkylphenol compound in the presence of a promoter.

19. The method according to claim 18, wherein the promoter is at least one compound selected from the group consisting of dialkyl sulfoxides, dialkyl formamides, dialkyl ethers, N,N-dialkyl acetamides, methyl ethyl ketone, methyl butyl ketone, phase transfer agents, crown ethers, and mixtures thereof.

20. The method according to claim 18, wherein the promoter is tetrahydrofuran.

21. A method for the production of a hindered phenolic alkyl ester compound of Formula I:

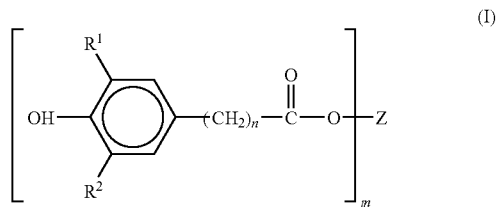

wherein:
  $R^1$ and $R^2$ are independently selected from the group consisting of H, alkyl, cycloalkyl, aryl, alkylaryl, and arylalkyl, where at least one of $R^1$ and $R^2$ is sterically bulky;
  n is 2; and
  Z is alkyl;
said method comprising the steps of:
  a) reacting methyl acrylate with an alkylphenol compound in the presence of a first catalyst to form a methyl ester intermediate compound, wherein the alkylphenol compound is in accordance with Formula II:

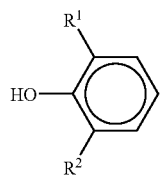

and wherein $R^1$ and $R^2$ are defined as above;
b) reacting an alcohol having at least 2 carbon atoms with the methyl ester intermediate compound in the presence of a second catalyst to form the hindered phenolic alkyl ester compound having the structure according to Formula I, and
c) forming a precipitated phosphate salt by steps consisting essentially of
i) neutralizing the catalyst residue with an aqueous phosphoric acid, and
ii) removing water to form a precipitated phosphate salt, and
d) separating the precipitated phosphate salt from the hindered phenolic alkyl ester compound,
wherein said first catalyst and said second catalyst are the same and comprise at least one compound selected from the group consisting of alkali metal hydroxides and alkali metal alkoxides, and mixtures thereof.

22. The method according to claim 21, wherein $R^1$ and $R^2$ are alkyl.

23. The method according to claim 21, wherein the aqueous phosphoric acid is aqueous orthophosphoric acid.

24. The method according to claim 21, wherein $R^1$ and $R^2$ are tert-butyl and wherein Z is butyl, isooctyl, or 2-ethylhexyl.

25. The method according to claim 21, wherein Z is $C_2$-$C_{20}$ alkyl.

26. The method according to claim 21 wherein the hindered phenolic compound is 2,6-di-tert-butylphenol, wherein the alcohol having at least 2 carbon atoms is n-butyl alcohol, isooctyl alcohol, or 2-ethylhexyl alcohol, and wherein the first catalyst and the second catalyst utilized in the method is potassium hydroxide.

27. The method according to claim 21, wherein the aqueous phosphoric acid comprises at least one compound selected from the group consisting of orthophosphoric acid ($H_3PO_4$), pyrophosphoric acid ($H_4P_2O_7$), metaphosphoric acid ($HPO_3$), and mixtures thereof.

28. The method in accordance with claim 21 wherein as charged to the reactor, the second catalyst has the same chemical composition as the first catalyst; wherein the first and second catalyst residues are neutralized with aqueous orthophosphoric acid to form a precipitated salt, and wherein said first catalyst and said second catalyst as charged to the reactor are the same and comprise potassium hydroxide or potassium alkoxide.

29. The method according to claim 18, wherein the promoter comprises at least one compound selected from the group consisting of dimethyl sulfoxide, dimethyl formamide, diethyl ether, diisopropyl ether, and mixtures thereof.

30. A method for the production of a hindered phenolic alkyl ester compound, which method comprises:
a) reacting methyl acrylate with a hindered alkylphenol in the presence of tetrahydrofuran and a first catalyst to form a methyl ester intermediate compound,
b) reacting an alcohol having at least 2 carbon atoms with the methyl ester intermediate compound in the presence of a second catalyst to form the hindered phenolic alkyl ester compound,
c) forming a precipitated salt by steps consisting essentially of
i) neutralizing any catalyst residue with an aqueous phosphoric acid, and
ii) removing water to form a precipitated salt, and
d) separating the precipitated salt from the hindered phenolic alkyl ester compound, wherein said first and said second catalyst are the same and comprise at least one compound selected from the group consisting of alkali and alkaline earth metal hydroxides and oxides, alkali metal hydrides, alkali metal alkoxides, alkali metal amides, alkali metal hydrocarbyloxides, and mixtures thereof.

31. The method according to claim 30, wherein the alcohol is reacted with the methyl ester intermediate compound in the presence of tetrahydrofuran.

32. A method for the production of a sterically hindered phenolic alkyl ester compound, which method comprises:
reacting an alkyl acrylate with a sterically hindered alkylphenol compound in the presence of a catalyst to form the hindered phenolic alkyl ester compound,
forming a precipitated salt by steps consisting essentially of
i) neutralizing the catalyst with an aqueous phosphoric acid, and
ii) removing water to form a precipitated salt, and separating the precipitated salt from the hindered phenolic alkyl ester compound by filtration,
wherein said catalyst comprises at least one compound selected from the group consisting of alkali metal hydroxides and alkali metal alkoxides.

33. The method according to claim 32, wherein the alkyl acrylate is methyl acrylate.

34. The method according to claim 32, wherein the alkyl acrylate is a high molecular weight alkyl acrylate.

35. The method according to claim 34, wherein the high molecular weight alkyl acrylate is a $C_2$-$C_{10}$ alkyl acrylate.

36. The method according to claim 35, wherein the $C_2$-$C_{10}$ alkyl acrylate is a compound selected from the group consisting of n-butyl acrylate, sec-butyl acrylate, n-octyl acrylate, 2-ethylhexyl acrylate, isoheptyl acrylate, isooctyl acrylate, isononyl acrylate, isodecyl acrylate, and mixtures thereof.

37. The method according to claim 32, wherein the hindered phenolic alkyl ester compound is formed in a liquid form.

38. The method according to claim 32, wherein the alkyl acrylate is reacted with the alkylphenol compound in the presence of an alcohol.

39. The method according to claim 38, wherein the alcohol is a high molecular weight alcohol.

40. The method according to claim 32, wherein the alkyl acrylate is reacted with the alkylphenol compound in the presence of a promoter.

41. The method according to claim 40, wherein the promoter comprises at least one compound selected from the group consisting of dialkyl sulfoxides, dialkyl formamides, dialkyl ethers, N,N-dialkyl acetamide, methyl ethyl ketone, methyl butyl ketone, phase transfer agents, crown ethers, and mixtures thereof.

42. The method according to claim 40, wherein the promoter is tetrahydrofuran.

43. The method according to claim 32, wherein the aqueous acid is orthophosphoric acid.

44. A method for the production of a hindered phenolic alkyl ester compound, said method consisting of:
   reacting an alkyl acrylate with a sterically hindered alkylphenol compound in the presence of a catalyst to form the sterically hindered phenolic alkyl ester compound,
   forming a precipitated salt by steps consisting essentially of
   i) neutralizing the catalyst residue with an aqueous phosphoric acid, and
   ii) removing water to form a precipitated salt, and separating the precipitated salt from the hindered phenolic alkyl ester compound by filtration,
   wherein said catalyst comprises at least one compound selected from the group consisting of alkali and alkaline earth metal hydroxides and oxides, alkali metal hydrides, alkali metal alkoxides, alkali metal amides, zinc salts, calcium salts, monoalkyltins, alkali metal hydrocarbyloxides, and mixtures thereof.

45. A method for the production of a hindered phenolic alkyl ester compound, which method comprises:
   a) reacting methyl acrylate with a hindered phenolic compound in the presence of a first catalyst to form a methyl ester intermediate compound,
   b) reacting an alcohol having at least 2 carbon atoms with the methyl ester intermediate compound in the presence of a second catalyst to form the hindered phenolic alkyl ester compound,
   c) forming a precipitated salt by steps consisting essentially of
   i) neutralizing any catalyst residue with an aqueous phosphoric acid or phosphorous acid, and
   ii) removing water to form a precipitated salt, and
   d) separating the precipitated salt from the hindered phenolic alkyl ester compound,
   wherein said first catalyst and said second catalyst as charged to the reactor are the same and comprise at least one compound selected from the group consisting of alkali and alkaline earth metal hydroxides and oxides, alkali metal hydrides, alkali metal alkoxides, alkali metal amides, alkali metal hydrocarbyloxides, and mixtures thereof.

46. A method for the production of a sterically hindered phenolic alkyl ester compound, which method comprises:
   I) reacting an alkyl acrylate with a sterically hindered alkylphenol compound in the presence of an alcohol and a catalyst to form the sterically hindered phenolic alkyl ester compound,
   II) forming a precipitated phosphate salt by steps consisting essentially of
   i) neutralizing any catalyst residue with an aqueous phosphoric acid, and
   ii) removing water to form a precipitated phosphate salt, and
   III) separating the precipitated phosphate salt from the sterically hindered phenolic alkyl ester compound,
   wherein said first catalyst and said second catalyst as charged to the reactor comprise at least one compound selected from the group consisting of alkali metal hydroxides, alkali metal alkoxides, and mixtures thereof.

47. A method as in claim 46 wherein the alkyl acrylate is methyl acrylate.

48. A method as in claim 46 wherein the alcohol is a high molecular weight alcohol.

49. A method as in claim 46 wherein the alkyl acrylate is reacted with the alkylphenol compound in the presence of a promoter.

50. A method as in claim 46 wherein the aqueous acid is orthophosphoric acid.

* * * * *

UNITED STATES PATENT AND TRADEMARK OFFICE
CERTIFICATE OF CORRECTION

| | | |
|---|---|---|
| PATENT NO. | : 7,667,066 B2 | Page 1 of 1 |
| APPLICATION NO. | : 10/788850 | |
| DATED | : February 23, 2010 | |
| INVENTOR(S) | : Gatto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 747 days.

Signed and Sealed this

Twelfth Day of October, 2010

David J. Kappos
*Director of the United States Patent and Trademark Office*